(12) United States Patent
Tournier (10) Patent No.: US 8,702,669 B2
(45) Date of Patent: Apr. 22, 2014

(54) DIAPER SHEATH WITH ADJUSTABLE SLIDE MECHANISM

(75) Inventor: Gaëlle Tournier, Kowloon (HK)

(73) Assignee: Pure Precision Limited, Tortola (VG)

( * ) Notice: Subject to any disclaimer, the term of this patent is extended or adjusted under 35 U.S.C. 154(b) by 84 days.

(21) Appl. No.: 13/157,190

(22) Filed: Jun. 9, 2011

(65) Prior Publication Data

US 2011/0301561 A1    Dec. 8, 2011

Related U.S. Application Data

(63) Continuation-in-part of application No. 12/723,036, filed on Mar. 12, 2010.

(30) Foreign Application Priority Data

Oct. 18, 2010   (CN) .......................... 2010 2 0587946

(51) Int. Cl.
   *A61F 13/49*   (2006.01)
   *A61F 13/493*  (2006.01)
   *A61F 13/68*   (2006.01)

(52) U.S. Cl.
   USPC ................. 604/385.14; 604/385.15; 604/394

(58) Field of Classification Search
   USPC ............. 604/385.14, 385.15, 385.24–385.27, 604/385.3, 393–395; 2/73, 76, 78.1, 78.3, 2/78.4, 111, 112, 217, 221, 237, 400, 2/401; D24/124–126
   See application file for complete search history.

(56) References Cited

U.S. PATENT DOCUMENTS 2,085,913 A * 7/1937 Lipton ............................. 2/237
2,664,895 A   1/1954 Shulman
(Continued)

FOREIGN PATENT DOCUMENTS

AU   2007211915 B2   3/2008
CA       2120840 A1  10/1995
(Continued)

OTHER PUBLICATIONS

"The Natural Baby Company" GroBaby™ product description downloaded from the World Wide Web at www.thenaturalbabyco.com/gro-baby-i-54.htm dated Jan. 11, 2010, 3 pages.

(Continued)

*Primary Examiner* — Jackie Ho
*Assistant Examiner* — Kathryn E Ditmer
(74) *Attorney, Agent, or Firm* — Miles & Stockbridge P.C.

(57) ABSTRACT

A diaper sheath having a shell with an inner panel and an outer panel forming a front edge, a back edge, a first side edge and a second side edge. The diaper sheath also includes a first intermediate pocket and a second intermediate pocket set along the first side edge and the second side edge respectively, each intermediate pocket having at least one opening. The diaper sheath further includes a first intermediate strip and a second intermediate strip set inside each of the first and second intermediate pockets respectively, the first and second intermediate strips each having an anchor portion attached to an attachment ring, and an elongated portion having a loop formed through a slide, the loop passing through the attachment ring and having a continuously adjustable length selected by moving the slide to a desired position along the elongated portion.

25 Claims, 9 Drawing Sheets

(56) References Cited

U.S. PATENT DOCUMENTS

| | | | |
|---|---|---|---|
| 2,969,065 | A | 1/1961 | Fransworth |
| 3,063,453 | A | 11/1962 | Brecht |
| 3,237,625 | A | 3/1966 | Johnson |
| 3,368,563 | A | 2/1968 | Scheier |
| 3,441,025 | A * | 4/1969 | Ralph ............... 604/398 |
| 3,459,186 | A | 8/1969 | Schwartz |
| RE26,912 | E | 6/1970 | Scheier |
| 3,529,600 | A | 9/1970 | Seltzer |
| 3,530,859 | A | 9/1970 | Heimowitz |
| 3,613,687 | A | 10/1971 | Kennedy |
| 3,828,785 | A | 8/1974 | Gamm et al. |
| 4,402,690 | A | 9/1983 | Redfern |
| 4,411,660 | A | 10/1983 | Dawn et al. |
| 4,573,987 | A | 3/1986 | Lamb |
| 4,643,726 | A | 2/1987 | Gegelys |
| 4,704,117 | A | 11/1987 | Mitchell |
| 4,718,902 | A | 1/1988 | Bonito |
| 4,847,134 | A | 7/1989 | Fahrenkrug et al. |
| 4,938,753 | A | 7/1990 | Van Gompel et al. |
| 4,961,982 | A | 10/1990 | Taylor |
| 4,978,345 | A | 12/1990 | Holliday et al. |
| 5,078,709 | A | 1/1992 | Siciliano |
| 5,114,418 | A | 5/1992 | Levy |
| 5,197,958 | A | 3/1993 | Howell |
| 5,261,900 | A | 11/1993 | Houle et al. |
| 5,290,269 | A | 3/1994 | Heiman |
| 5,306,267 | A | 4/1994 | Hahn et al. |
| D352,353 | S * | 11/1994 | Silver ............... D24/126 |
| 5,368,585 | A | 11/1994 | Dokken |
| 5,389,093 | A | 2/1995 | Howell |
| 5,403,303 | A | 4/1995 | Beplate |
| 5,613,959 | A | 3/1997 | Roessler |
| 5,891,122 | A | 4/1999 | Coates |
| 6,155,083 | A | 12/2000 | Goeser et al. |
| 6,402,586 | B1 * | 6/2002 | Winik et al. ............... 450/78 |
| 6,423,047 | B1 | 7/2002 | Webster |
| 6,579,273 | B2 | 6/2003 | Dupuy |
| 6,610,381 | B1 | 8/2003 | Conway |
| 6,705,128 | B1 | 3/2004 | Sciacca |
| 6,782,557 | B1 | 8/2004 | Feder |
| 6,806,214 | B2 | 10/2004 | Li et al. |
| 6,895,603 | B2 | 5/2005 | Coates |
| D528,739 | S * | 9/2006 | Williamson ............... D2/712 |
| 7,438,707 | B2 | 10/2008 | Bushman et al. |
| 7,491,196 | B2 | 2/2009 | Franke et al. |
| 7,629,501 | B2 | 12/2009 | Labit et al. |
| 7,678,094 | B1 | 3/2010 | Cannon et al. |
| 7,685,652 | B2 * | 3/2010 | Digney ............... 2/406 |
| 7,686,796 | B2 | 3/2010 | Kuen et al. |
| 7,875,014 | B2 | 1/2011 | Hendren et al. |
| 7,914,507 | B1 | 3/2011 | Magee |
| 7,993,322 | B2 | 8/2011 | Brud et al. |
| 8,062,276 | B2 | 11/2011 | Labit et al. |
| 8,262,635 | B2 | 9/2012 | Labit et al. |
| 2001/0015600 | A1 * | 8/2001 | Duong et al. ............... 312/351.1 |
| 2002/0010452 | A1 | 1/2002 | Dupuy |
| 2003/0181885 | A1 | 9/2003 | Harkness |
| 2004/0122392 | A1 | 6/2004 | Seneviratne |
| 2005/0148980 | A1 | 7/2005 | Fitton |
| 2005/0210560 | A1 | 9/2005 | Coates |
| 2006/0167432 | A1 | 7/2006 | Sigari |
| 2007/0277282 | A1 | 12/2007 | Sheppell |
| 2008/0065039 | A1 | 3/2008 | Labit et al. |
| 2008/0215027 | A1 | 9/2008 | Labit et al. |
| 2008/0215028 | A1 | 9/2008 | Brown et al. |
| 2009/0187156 | A1 | 7/2009 | Anzalone |
| 2009/0240228 | A1 | 9/2009 | Nonnenmann |
| 2010/0087794 | A1 | 4/2010 | Labit et al. |
| 2012/0172827 | A1 | 7/2012 | Dupuy |

FOREIGN PATENT DOCUMENTS

| | | |
|---|---|---|
| CN | 2 313 397 Y | 4/1999 |
| CN | 2479752 Y | 3/2002 |
| FR | 1 020 225 | 6/1950 |
| GB | 2452052 A | 2/2009 |
| GB | 2468724 A | 9/2009 |
| NZ | 549433 | 7/2008 |
| WO | WO 90/06066 A1 | 6/1990 |
| WO | WO 98/29080 A1 | 7/1998 |
| WO | WO 2008/030984 A2 | 3/2008 |

OTHER PUBLICATIONS

"Rump•a•rooz®" product description downloaded from the World Wide Web at www.rumparooz.com dated May 14, 2008, 3 pages.

"Rump•a•rooz®" G2 product description downloaded from the World Wide Web at www.rumparooz.com/catalog.php?category=65 dated Dec. 7, 2009, 3 pages.

"FuzziBunz™ Features" product description downloaded from the World Wide Web at www.fuzzibunzasia/fuzzi_details.php dated Apr. 6, 2009, 1 page.

"FuzziBunz™ One Size Diapers—Grows with Baby" product description downloaded from the World Wide Web at www.fuzzibunzasia/one_size_diaper.php dated Apr. 4, 2009, 1 page.

"Why Choose FuzziBunz™" description downloaded from the World Wide Web at www.fuzzibunzasia/why_choose_fuzzibunz.php dated Apr. 6, 2009, 1 page.

"Cotton Babies®" product description downloaded from the World Wide Web at www.cottonbabies.com/product_info.php?cPath=98&products_id=1279 dated Jan. 26, 2009, 7 pages.

Office Action issued Jul. 6, 2012, in U.S. Appl. No. 12/723,036.

Response to EPO Communication filed Mar. 23, 2012, in European Patent Application No. 10707835.4.

Response to Chinese Office Action filed Aug. 21, 2012, in Chinese Patent Application No. CN201010114228.5 (and translation thereof).

Notification of the First Office Action date of dispatch Jun. 25, 2013, for Chinese Patent Application No. 201110286417.5 (and translation thereof).

Notification of Second Office Action date of dispatch Dec. 14, 2012, for Chinese Patent Application No. 201010114228.5 (and translation thereof).

EPO Communication dated Nov. 6, 2012, for European Patent Application No. 10707835.4.

Response to EPO Communication filed Mar. 18, 2013, for European Patent Application No. 10707835.4.

Response to EPO Communication filed Aug. 8, 2013, for European Patent Application No. 10707835.4.

Demand and amended claims filed with the EPO on Apr. 9, 2013, for PCT/EP2011/064882.

International Preliminary Report on Patentability date of completion Nov. 7, 2013, for PCT/EP2011/064882.

Written Opinion of the IPEA date of mailing Jul. 22, 2013, for PCT/EP2011/064882.

Amended claims filed with the EPO on Sep. 20, 2013, for PCT/EP2011/064882.

Office Action dated Dec. 30, 2013 for U.S. Appl. No. 12/723,036.

Office Action dated Dec. 16, 2013 for Australian Patent Application No. 2011218650.

* cited by examiner

DIAPER SHEATH WITH ADJUSTABLE SLIDE MECHANISM

CROSS-REFERENCE TO RELATED APPLICATION

This application is a continuation-in-part of U.S. application Ser. No. 12/723,036, filed Mar. 12, 2010, the entire disclosure of which is hereby incorporated herein by reference.

FIELD

The present invention relates generally to diapers, and more particularly to a diaper having continuously adjustable leg openings.

BACKGROUND

Presently, diapers for infants (or others such as children, adults or animals) include cloth diapers, disposable diapers and all-in-one diapers. The manufacture, use and disposal of any diaper presents health and sanitation issues, energy and environmental cost issues and economic issues.

In addition to the above issues, another consideration can be the comfort of the diaper wearer. A diaper needs to be snug enough to ensure retention of solid and liquid waste and to prevent leakage, but not so snug as to be uncomfortable or hamper blood circulation in the wearer's legs or torso, or to create high humidity or moisture within the diaper. Discomfort or hampering of blood circulation can be caused by conventional, nonadjustable elastic leg openings. The hook and loop fasteners provided on conventional diapers may only allow for waist band adjustment may not provide for adjustment of the leg openings.

Conventional diapers with leg opening adjusting members may have an area contacting the skin of the wearer that is too large. Also, the material of some conventional adjustment members may be hard and uncomfortable for the wearer.

SUMMARY

The present invention was conceived in light of the above technical problems and limitations, among other things. An embodiment can include a diaper sheath having a shell made up of an inner panel and an outer panel, each having a front portion and a back portion. The inner and outer panels can be attached together peripherally in matched contour to form a front edge, a back edge, a first side edge and a second side edge. The diaper sheath can also include a front fastener attached to the front portion of the outer panel and a back fastener attached to the back portion of the inner panel. The back fastener can be cooperatively fastenable with the front fastener.

The diaper sheath can also include two intermediate pockets set along the two side edges respectively. Each intermediate pockets can have at least one opening. Two intermediate strips can be set inside each of the intermediate pockets respectively, and at least one end of each intermediate strip can be pulled outside of the intermediate pocket through the intermediate pocket opening. Fastening members can be set on the diaper sheath and fixed onto the intermediate strip.

The openings can be located in the middle portion of the intermediate pocket and a portion of the intermediate strip can be exposed outside the intermediate pockets through the intermediate pocket openings. Also, the diaper sheath can include an intermediate pocket flap positioned at the opening of each intermediate pocket, such that the intermediate pocket openings are covered by the intermediate pocket flaps.

In another embodiment, two intermediate pocket openings are provided on each intermediate pocket, and ends of the intermediate strip can pass through each of the intermediate pocket openings.

In another embodiment, one end of each intermediate strip can pass through the intermediate pocket opening, while the other end is fixed inside the intermediate pocket.

The diaper sheath can also include a front opening disposed on the front portion of the inner panel covered by a front flap attached to the front portion of the inner panel.

In another embodiment, the intermediate strips and the opening of the intermediate pocket can be covered by the front flap.

In yet another embodiment, the back portion of the inner panel has a back opening and a back flap attached to the back portion of the inner panel covers the back opening. The intermediate strips and the intermediate pocket opening can be covered by the back flap.

In still another embodiment, the fastening member is an intermediate button attached disposed on the diaper sheath and attached along each of the two side edges. Each intermediate strip can have at least one intermediate hole on it and the intermediate button can be cooperatively fastenable with the intermediate hole, or one of the intermediate holes. Each intermediate button can be set on the inner surface of the intermediate pockets.

In another embodiment, the fastening member is a stopper and each intermediate strip is inserted through the stopper so that the effective length of the intermediate strip can be continuously adjusted by disengaging the stopper mechanism, pulling a portion of the intermediate strip through the stopper and reengaging the stopper mechanism at the desired point on the intermediate strip. The stoppers can be placed within the intermediate pocket or located at the opening of the intermediate pocket.

In yet another embodiment, the fastening member is a front snap and the intermediate strip includes at least one back snap that is cooperatively fastenable with the front snap.

The inner panel can include a laminated liquid permeable material, while the outer panel can include a laminated liquid impervious material. The laminated liquid impervious material can be a layer of laminated organic cotton on the outer surface of the outer panel. The inner panel can be formed from a fleece material made of 100% polyester.

In still another embodiment, the diaper sheath can include a back elastic strip attached to the inner and outer panels along the edge of the back portion. A back button attached along the edge of the back portion can be cooperatively fastenable to at least one back hole in the back elastic strip so as to provide a waist size adjustment mechanism. The back fastener can be attached to both ends of the back portion of the inner panel.

In another embodiment, a front fastener can include a front plurality of snaps. The back fastener can include a plurality of back snaps each cooperatively fastenable with one of the front plurality of snaps.

The intermediate strip can be elastic band, string, rope, thread or other suitable material. The diaper sheath can include two measuring indicators set on each of the intermediate strips respectively. The measuring indicator can be scale marks, numbers, letters or any other suitable measuring indicators. In an embodiment with holes in the intermediate strips, the measuring indicator can be disposed beside the intermediate hole, or holes. In various embodiments, the intermediate strips are solid and do not have holes.

Still another embodiment includes a diaper having a diaper sheath according to at least one embodiment and a pad that can be fully or partially inserted between the inner and outer panels. The pad can be a removable, reusable, and/or absorbent pad. The pad can also be a disposable pad.

One or more embodiments can provide:
(1) leg openings having a size that can be adjusted by moving a respective adjustment member to a desired location on each intermediate strip in the diaper sheath of the present invention, so the diaper can be more comfortable for the wearer;
(2) an intermediate pocket flap, front flap or back flap that can cover the intermediate strips inside the diaper sheath so that the intermediate strips and adjustment members do not contact the skin of the wearer directly and therefore can help reduce or eliminate any uncomfortable feeling; and
(3) a way to accurately and quickly determine the proper position of the adjustment members using measuring indicators on the intermediate strip.

BRIEF DESCRIPTION OF THE DRAWINGS

For a further understanding of the present invention, reference should be made to the following detailed description taken in conjunction with the accompanying drawings, wherein.

DETAILED DESCRIPTION

Figure 1:
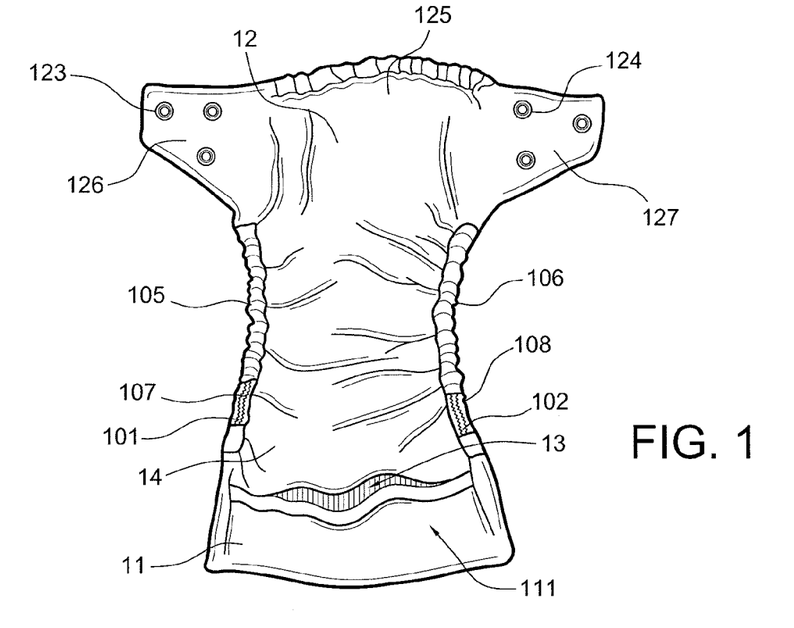
FIG. 1 is an inside view of an exemplary diaper sheath in accordance with at least one embodiment.
Figure 2:
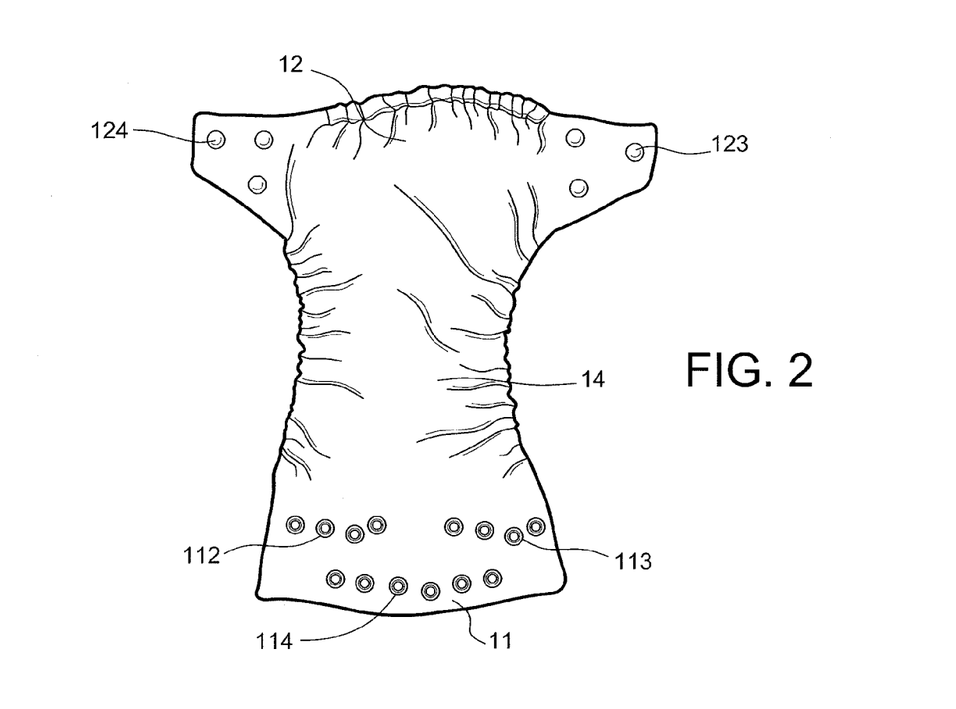
FIG. 2 is an outside view of an exemplary diaper sheath in accordance with at least one embodiment.
Figure 3:
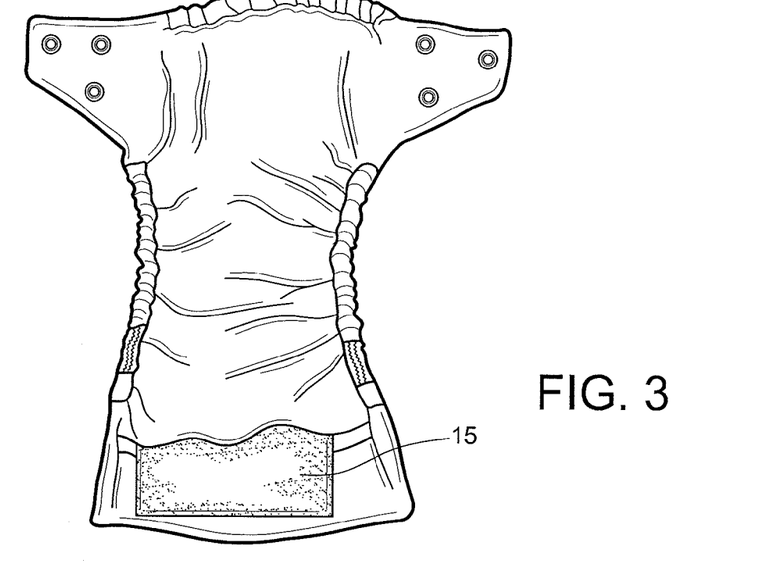
FIG. 3 is an inside view of an exemplary diaper sheath showing a pad in accordance with at least one embodiment.

An exemplary diaper is shown in FIGS. 1 and 2 as viewed from the inside and outside, respectively. In particular, the diaper includes an inner panel and an outer panel, each inner and outer panel having a front portion 11 and a back portion 12 connected by an intermediate portion 14. The front portion 11 of the inner panel has a front opening 13. The inner and outer panels are attached together peripherally in matched contour. The back portion 12 has two elongated wings 126, 127. The front portion 11 has a plurality of front snaps 112, 113, 114 attached to the front portion 11 of the outer panel. The back portion 12 has a plurality of back snaps 123, 124 attached to the two elongated wings 126, 127, respectively. Each of the plurality of back snaps 123, 124 is cooperatively fastenable with one of the front snaps 112, 113, 114.

The diaper also includes a front flap 111 attached to the front portion 11 of the inner panel. The front opening 13 is covered by the front flap 111. The diaper also includes two intermediate pockets 105, 106, which are set (or disposed) along respective side edges of intermediate portion 14. There is one intermediate pocket opening 107, 108 on each respective intermediate pocket 105, 106. As shown in this embodiment, the intermediate pocket openings 107, 108 are set in the middle portion of the intermediate pockets 105, 106. The diaper also includes intermediate elastic strips 101, 102, one end of which are loosely hidden inside the intermediate pockets 105, 106 and can go through the intermediate strip openings 107, 108. The portion of the intermediate strips 101, 102 that are positioned at the intermediate pocket openings 107, 108 can be exposed outside the intermediate pockets 105, 106. The intermediate strips 101, 102 can be elastic bands or other elastic or stretchable material. Alternatively, the intermediate strips 101, 102 can be ropes, threads, strings or other material not having elasticity.

Also, the intermediate pocket openings 107, 108 can be formed narrow, so that intermediate strips 101,102 will not be exposed outside the intermediate pockets 105, 106.

The diaper can include intermediate buttons 103, 104 disposed on the inner surface of the intermediate pockets 105, 106.

Figure 4:
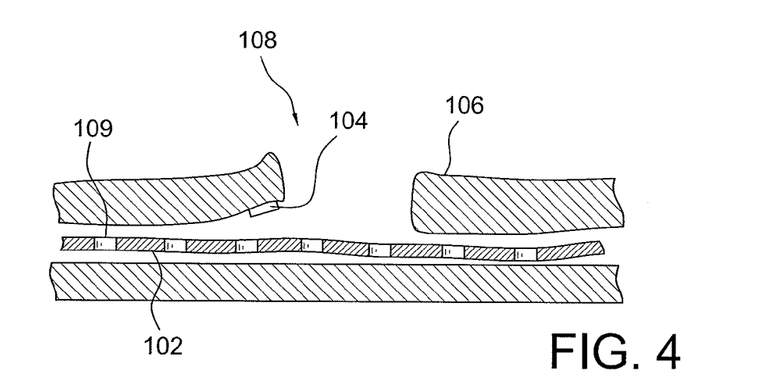
FIG. 4 is a cross-sectional view of an exemplary intermediate strip in accordance with at least one embodiment.
Figure 5:
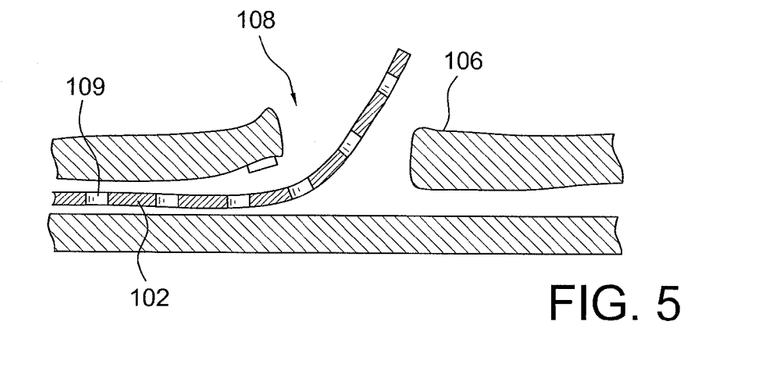
FIG. 5 is a cross-sectional view of an exemplary intermediate strip in accordance with at least one embodiment.

Taking the intermediate pocket 106 on one side as an example, as shown in FIGS. 4 and 5, the intermediate strip 102 can have a plurality of intermediate holes 109 set in a spaced apart arrangement. The intermediate button 104 is cooperatively fastenable with one of the intermediate holes 109. During usage, a user can draw the intermediate strip 102 out via the intermediate pocket opening 108, fasten the suitable intermediate hole 109 onto the intermediate button 104, and put the loose end of the intermediate strip 102 back into the intermediate pocket 106 via the intermediate pocket opening 108. By adjusting the position on the intermediate strips 101, 102 where the intermediate button is fastened, the extension of the elastic leg line can be easily adjusted, the diaper sheath can be more fitting with the skin of the baby and more comfortable for the baby.

Figure 6:
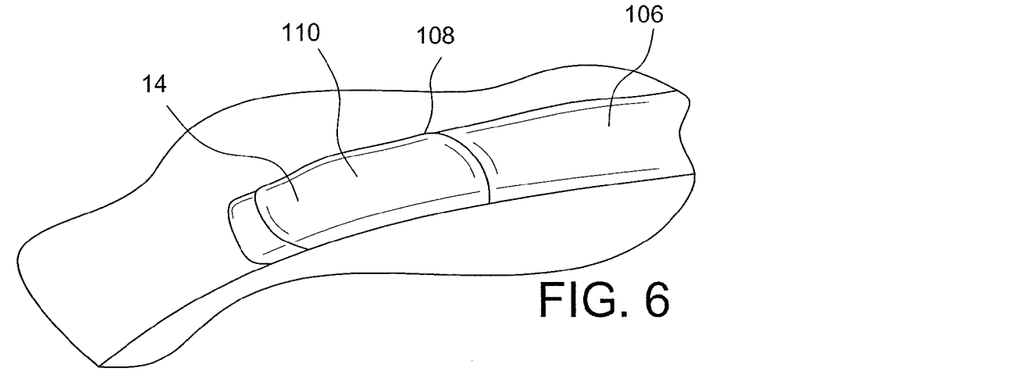
FIG. 6 is a view of an exemplary intermediate pocket flap in accordance with at least one embodiment.
Figure 7:
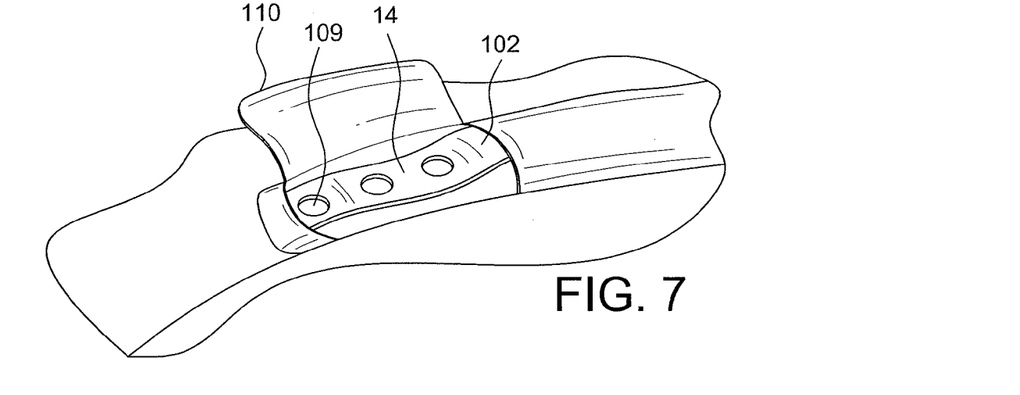
FIG. 7 is a view of an exemplary intermediate pocket flap in accordance with at least one embodiment.

In another embodiment of this invention, there is an intermediate pocket flap 110 on each intermediate pocket opening 107, 108 that covers the portion of intermediate strips 101, 102 (refer to FIGS. 6 and 7) exposed outside the intermediate strips 101, 102. This structure can also prevent the intermediate strips 101, 102 from contacting the skin of the babies directly, possibly causing an uncomfortable feeling.

Figure 8:
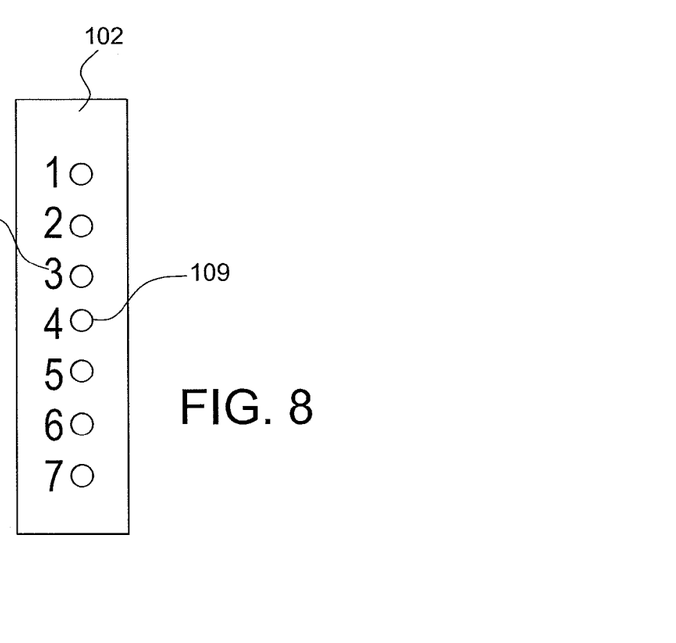
FIG. 8 is a view of an exemplary measuring indicator in accordance with at least one embodiment.
Figure 9:
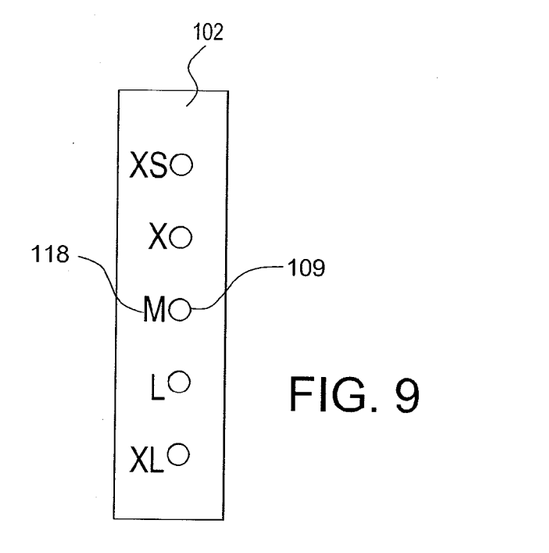
FIG. 9 is a view of an exemplary measuring indicator in accordance with at least one embodiment.
Figure 10:
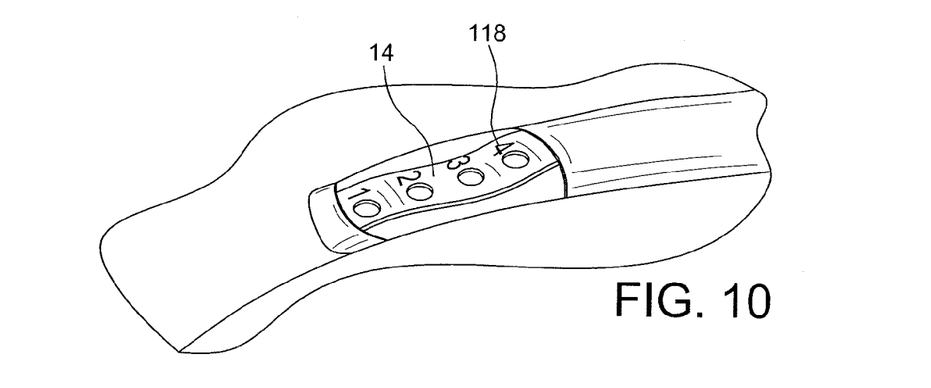
FIG. 10 is a view of an exemplary intermediate strip with the measuring indicator in accordance with at least one embodiment.
Figure 11:
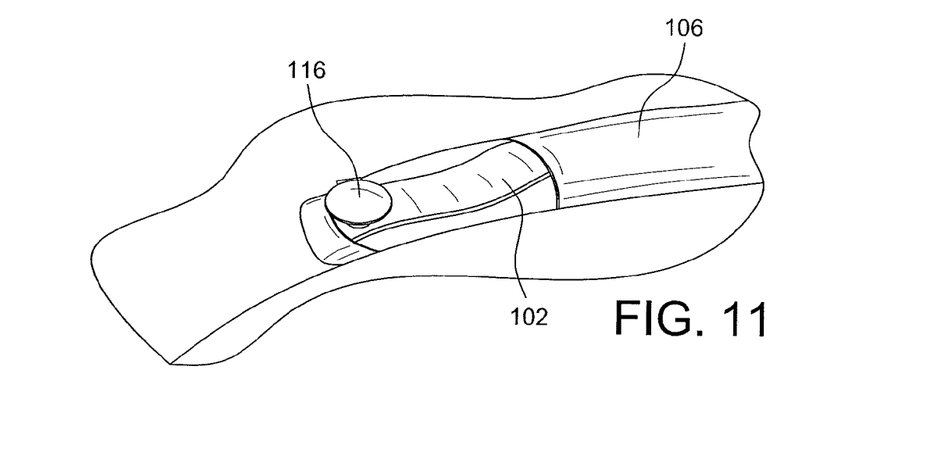
FIG. 11 is a view of an exemplary intermediate pocket with a stopper in accordance with at least one embodiment.

Each of the intermediate strips 101, 102 can also include a measuring indicator 118 (refer to FIGS. 8-10), when the intermediate hole 109 is fastened onto the intermediate button (e.g., 104), the measuring indicator 118 is placed beside the intermediate button to show the currently used size of the legline. A user can adjust the position of the elastic strips 101, 102 to fit their baby perfectly by simply changing the elastic position. The measuring indicator 118 can include numbers, letters, scale marks or any other indication that can show the size setting of the intermediate strip.

The diaper sheath can also include a back elastic strip 125 attached to the inner and outer panels along the edge of the back portion that can make the intermediate portion 14 and back portion 12 adjustable.

The diaper sheath according to various embodiments may further comprise a back button attached along the edge of the back portion. The back elastic strip can have at least one button holes cooperatively fastenable with the back button.

In addition, the diaper sheath can include a back flap attached to the back portion of the inner panel. Through the front flap and the back flap, the absorbent pad 15 can be held better. Similarly, in other embodiments, the back flap can also be used to cover the intermediate strip or the intermediate pockets opening, to prevent the directly contacting to the skin of the babies (see, e.g., FIGS. 16-19). The diaper can also include a back opening covered by the back flap.

Figure 13:
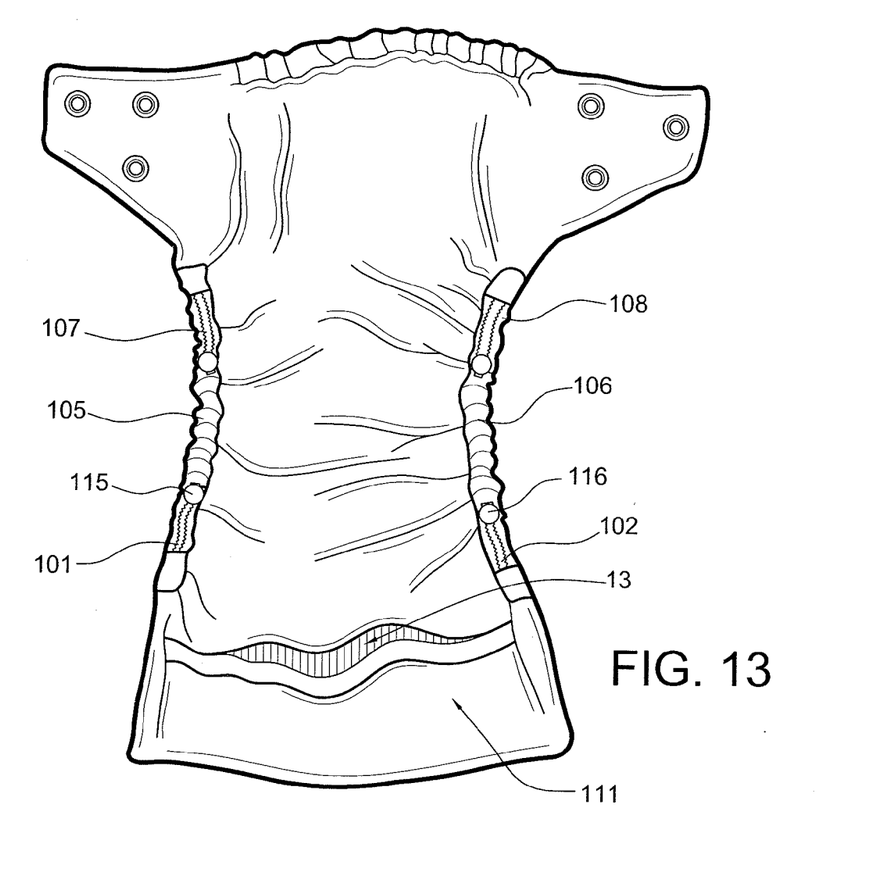
FIG. 13 is a view of an exemplary diaper sheath in accordance with at least one embodiment.
Figure 14:
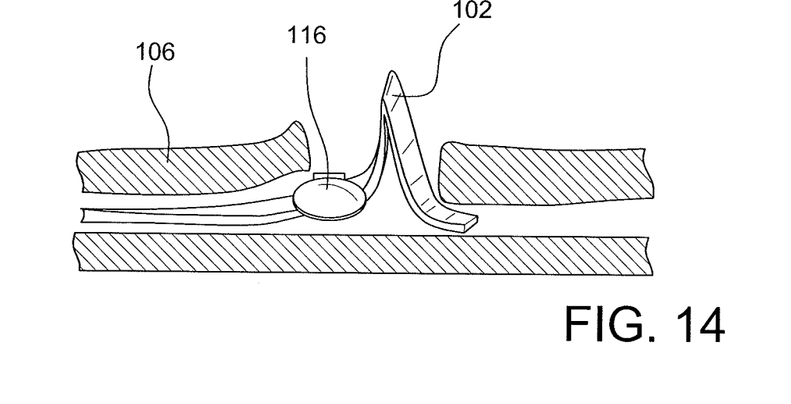
FIG. 14 is a cross-sectional view of an exemplary intermediate strip with a stopper in accordance with at least one embodiment.

As shown in FIG. 13, there are two intermediate pocket openings 107, 108 on each of the intermediate pockets 105, 106. Both ends of the intermediate strips 101, 102 can be loosely hidden inside the intermediate pockets 105, 106, and can go through the intermediate pocket openings 107, 108. Two stoppers 115,116 are equipped on each of the intermediate strips 101, 102, which extend through the stoppers 115, 116. The stoppers 115, 116 can slide along the intermediate strips 101, 102 and stick onto the intermediate pocket opening 107, 108. During usage, the parents of the babies can adjust the position of the stoppers 115, 116 to tighten or release the intermediate strips 101,102, so the elasticity of the intermediate strips 101, 102 can be adjusted.

The stopper 115, 116 can be a spring-loaded stopper or toggle. When a button on the stopper is pressed down, the stopper can freely slide along the intermediate strip; and when the button is released, the stopper grips the intermediate strip under force of a spring-loaded mechanism and the position of the stopper (and the effective length of the intermediate strip) is fixed. However, in various embodiments, the intermediate strip is not detachable from the stopper, and vice versa.

The stoppers 115, 116 and the intermediate strips 101, 102 can be covered by intermediate pocket flaps 110, a front flap 111 or a back flap so that the stoppers 115, 116 will not contact the skin of the wearer directly. The intermediate pocket openings 107, 108 can be formed narrow so that the intermediate strips 101, 102 will not be exposed outside the intermediate pockets 105, 106, and the stoppers 115, 116 can be set inside the intermediate pockets 105, 106 as well.

In another embodiment of this invention, one end of each intermediate strip 101, 102 is fixed inside the intermediate pockets 105, 106, while the other end is loosely hidden inside the intermediate pockets 105, 106. In a further embodiment of this invention, both ends of each intermediate strip 101, 102 can be fixed within the intermediate pockets 105, 106.

Figure 12:
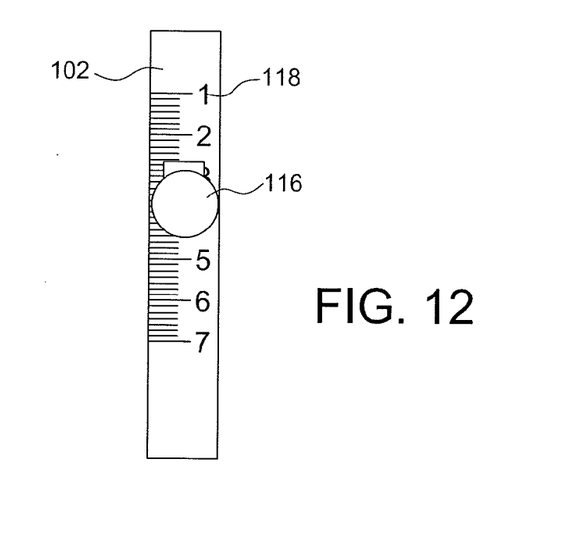
FIG. 12 is a view of an exemplary intermediate strip with a stopper in accordance with at least one embodiment.

In this embodiment, the measuring indicator is s series of scale marks on the intermediate strips 101, 102 (refer to FIG. 12). A user of the diaper can adjust the diaper quickly and accurately using the scale marks. Of course, the scale marks can be numbers, letters or other indicia as discussed above regarding FIGS. 8-10.

Comparing with the intermediate button 103, 104 and the intermediate holes 109, the setting of the stoppers 115, 116 has the advantage that the leg opening adjustment can be more flexible, and is not restricted by the distance internals between the intermediate holes 109. In other words, the stoppers provide for continuously adjustable intermediate strips.

Figure 15:
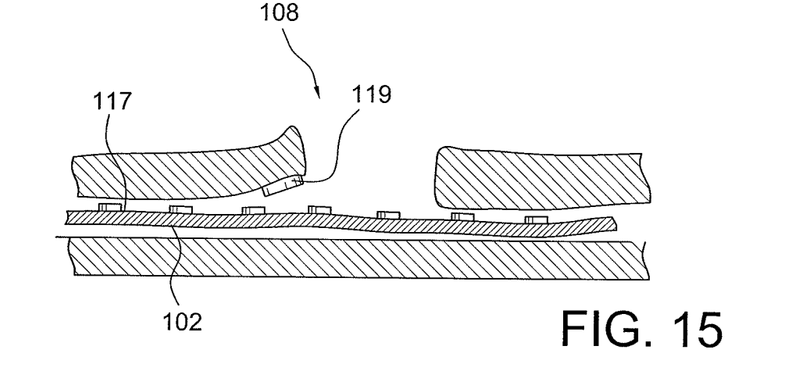
FIG. 15 is a cross-sectional view of an exemplary intermediate pocket comprising front and back snaps in accordance with at least one embodiment.

As shown in FIG. 15, in some embodiments the intermediate button 103, 104 is replaced by a front snap 119, and the intermediate holes 109 are replaced by plural back snaps 117 on each of intermediate strips 101, 102. The intermediate strips can adjust the leg openings of the diaper sheath by fastening the front snap 119 to a desired one of the back snaps 117.

Figure 16:
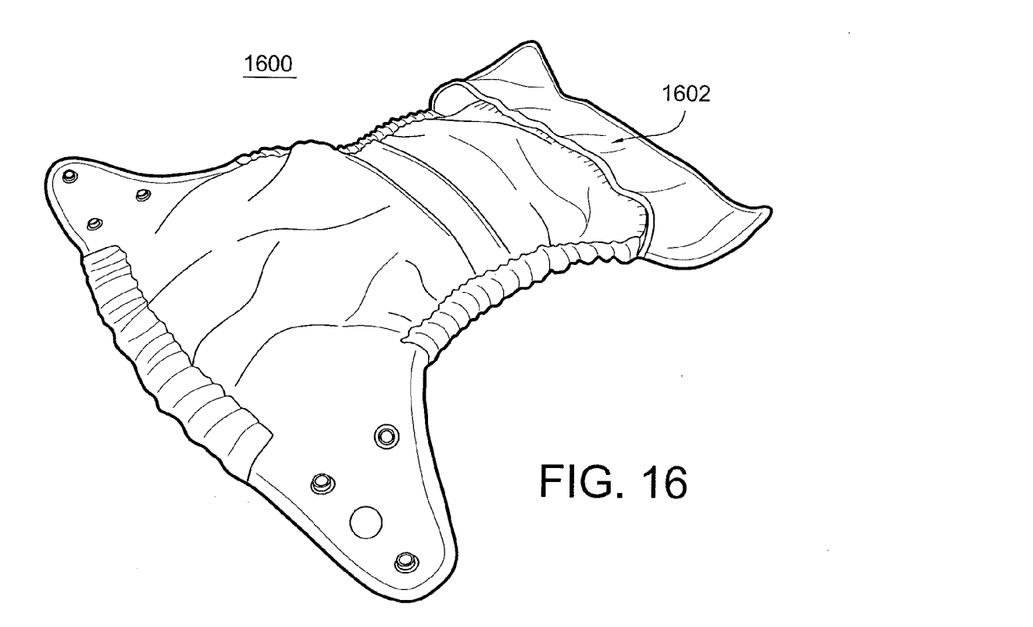
FIG. 16 is an outside view of an exemplary diaper sheath with an outside front flap and opening in accordance with at least one embodiment.
Figure 17:
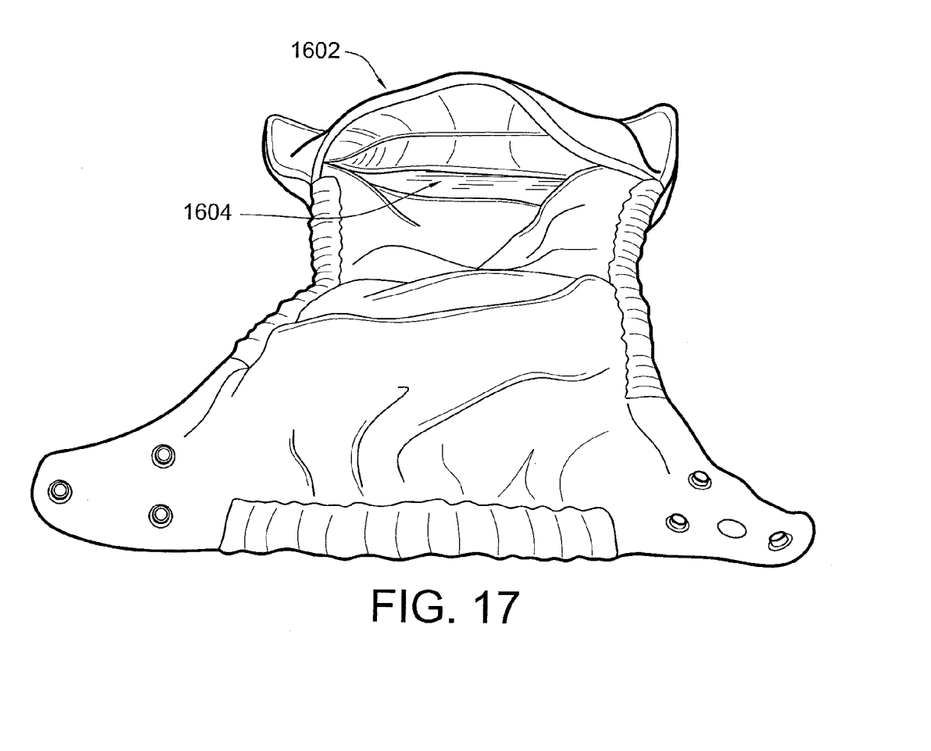
FIG. 17 is an outside view of an exemplary diaper sheath with an outside front flap open showing the interior of a front opening in accordance with at least one embodiment.

FIGS. 16-19 show an embodiment in which the intermediate strips are disposed under a front flap, which can prevent the intermediate strips from contacting the skin of the babies directly and possibly causing discomfort. FIGS. 16 and 17 show a diaper 1600 with a front flap 1602 covering a front opening 1604.

Figure 18:
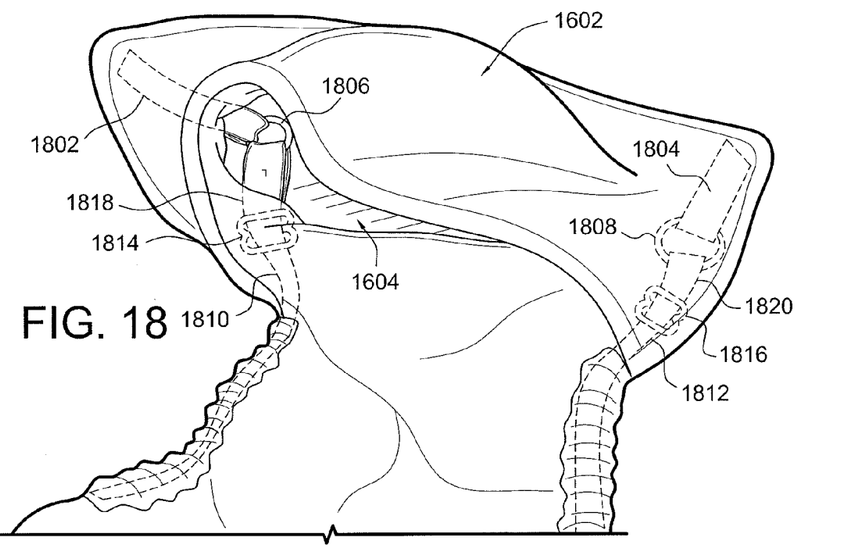
FIGS. 18 and 19 are views of an exemplary diaper sheath showing continuously adjustable leg opening adjustment members disposed for access from within a front opening in accordance with at least one embodiment.

FIG. 18 shows anchor intermediate strip portions 1802 and 1804 attached to respective rings 1806 and 1808. Elongated intermediate strip portions 1810 and 1812 extend through respective clips 1814 and 1816 several times to form loops 1818 and 1820. Loops 1818 and 1820 can be changed in size/length by moving elongated intermediate strip portions (1810, 1812) through respective clips (1814, 1816) in different directions, in a well known manner. However, the elongated intermediate strip portions 1810, 1812 are not detachable from the clips 1814, 1816 or the loops 1818, 1820. By using the looped strip and slide adjustment mechanism, a diaper in accordance with at least one embodiment can provide continuously adjustable diaper leg openings to provide a true "one size fits all" diaper. Also, as an alternative to the clips shown, other kinds of clips, e.g. a clip similar to the front part of the crocodile clip could be used. The clips can be relatively thin. Moreover, each leg opening is independently adjustable and can accommodate a wearer having different sized legs.

The intermediate strips used in some embodiments (e.g., the stopper, and loop and slide embodiments, or any not incorporating a button fastener) can be formed from elastic strips that have no holes or openings. The placement and shape of the rings 1806 and 1808 is an example for illustration purposes. It will be appreciate that the rings can be other shapes (such as D, or square) and also placed in other locations.

Figure 19:
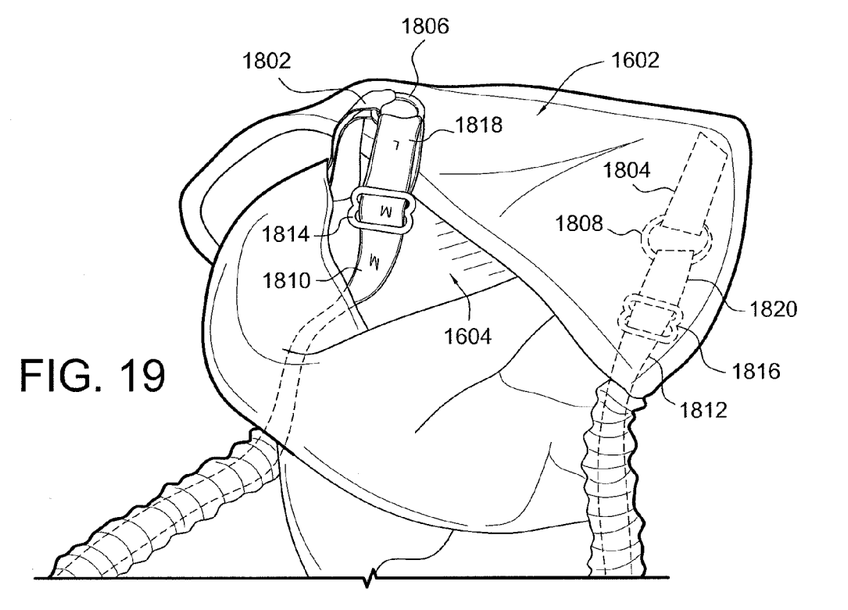

As shown in FIG. 19, an anchor intermediate strip and a corresponding elongated intermediate strip with clip can be temporarily pulled from the front opening 1604 to facilitate with adjustment and then returned to the front opening 1604 and covered by the front flap 1602.

It will be appreciated that while FIGS. 18 and 19 show a slide and looped strip adjustment member, the adjustment member can be a spring-loaded stopper, spring-loaded toggle or other suitable adjustment device. Also, the stopper may be a non-spring-loaded stopper.

In at least one other embodiment, the elongated intermediate strip portions 1810 and 1812, clips 1814 and 1816, and loops 1818 and 1820 are disposed on sides of intermediate portion 14.

Figure 20:
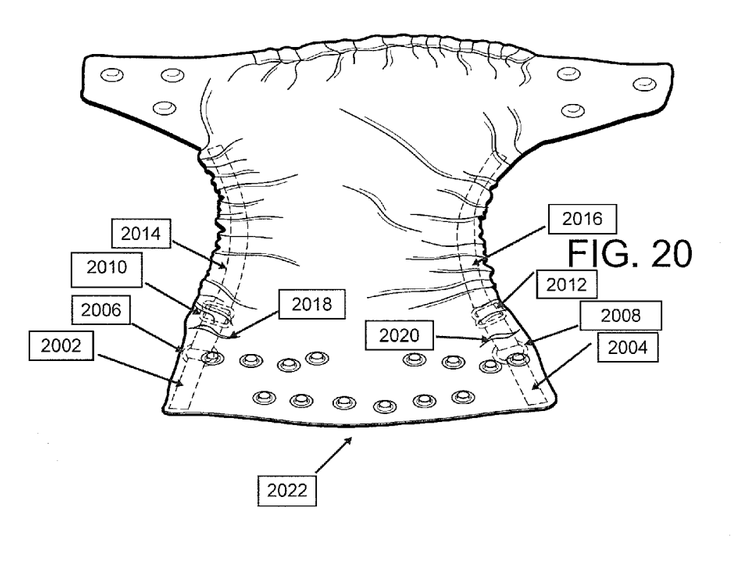
FIGS. 20 and 21 are views of an exemplary diaper sheath showing continuously adjustable leg opening adjustment members disposed for access from exterior front openings in accordance with at least one embodiment.
Figure 21:
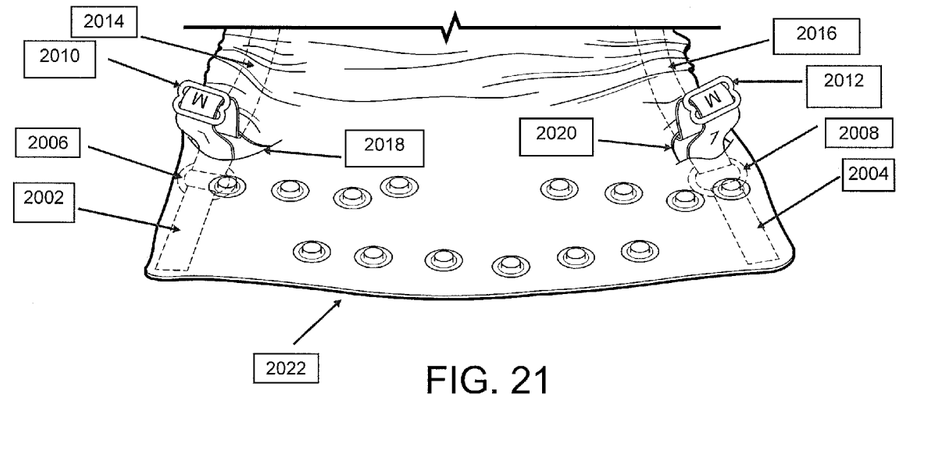

FIGS. 20 and 21 are views of an exemplary diaper sheath showing continuously adjustable leg opening adjustment members disposed for access from exterior front openings in accordance with at least one embodiment. In particular, the diaper sheath shown in FIGS. 20 and 21 includes shows anchor intermediate strip portions 2002 and 2004 attached to respective rings 2006 and 2008. Elongated intermediate strip portions 2014 and 2016 extend through respective clips 2010 and 2012 several times to form loops that wrap around each respective ring. The clips 2010 and 2012 can be accessed through slots 2018 and 2020, respectively. The loops can be changed in size/length by moving elongated intermediate strip portions (2014, 2016) through respective clips (2010, 2012) in different directions, in a well known manner. However, the elongated intermediate strip portions 2014, 2016 are not detachable from the clips 2010, 2012 or the loops. By using the looped strip and slide adjustment mechanism, a diaper in accordance with at least one embodiment can provide continuously adjustable diaper leg openings to provide a true "one size fits all" diaper. Moreover, each leg opening is independently adjustable and can accommodate a wearer having different sized legs.

In contrast to the embodiment shown in FIGS. 18 and 19, the embodiment shown in FIGS. 20 and 21 has the intermediate strips and adjustment clips disposed on the front, exterior side 2022 of the diaper sheath. In addition to being accessible through the slots, an embodiment with front accessible intermediate strips could include a flap and opening similar to that shown in FIGS. 16-19 to cover the intermediate strips.

FIG. 21 shows how the intermediate strips and clips can be temporarily pulled through the slots 2018 and 2020 in order to adjust the lengths of the intermediate strips.

The intermediate strips used in some embodiments (e.g., the stopper, and loop and slide embodiments, or any not incorporating a button fastener) can be formed from elastic strips that have no holes or openings.

It will be appreciated that the openings, slots or access panels for the intermediate strip adjustment clips can be located on the interior or exterior of the diaper sheath and also disposed at any point along the intermediate strip or leg opening from the front to the back of the diaper sheath.

While the invention has been described in conjunction with a number of embodiments, it is evident that many alternatives, modifications and variations would be or are apparent to those of ordinary skill in the applicable arts. Accordingly, Applicant intends to embrace all such alternatives, modifications, equivalents and variations that are within the spirit and scope of the invention.

What is claimed is:

1. A diaper sheath comprising:
   a shell having an inner panel and an outer panel, each of said inner and outer panels having a front portion and a back portion, each of said panels attached peripherally one to the other in matched contour to form a front edge, a back edge, and a first side edge and a second side edge;
   a first intermediate pocket and a second intermediate pocket set along the first side edge and the second side edge respectively, each intermediate pocket having at least one opening; and
   a first intermediate strip and a second intermediate strip set inside each of the first and second intermediate pockets respectively, the first and second intermediate strips each having an anchor portion attached to an attachment ring, and an elongated portion having a loop formed through a slide, the loop passing through the attachment ring and having a continuously adjustable length selected by moving the slide to a desired position along the elongated portion.

2. The diaper sheath of claim 1, wherein at least one of the openings of each said intermediate pocket is set in a substantially middle portion of the intermediate pocket.

3. The diaper sheath of claim 1, wherein a portion of said first intermediate strip and said second intermediate strip is exposed outside said intermediate pockets through the intermediate pocket openings.

4. The diaper sheath of claim 3, further comprising intermediate pocket flaps positioned at said intermediate pocket openings of the intermediate pockets, said intermediate pocket openings being covered by said intermediate pocket flaps.

5. The diaper sheath of claim 1, wherein there are two intermediate pocket openings on each intermediate pocket.

6. The diaper sheath of claim 1, wherein said front portion of the inner panel has a front opening disposed thereon.

7. The diaper sheath of claim 6, further comprising a front flap attached to said front portion of said inner panel, wherein said front opening is covered by said front flap.

8. The diaper sheath of claim 1, wherein the intermediate strips and the intermediate pocket openings are covered by the front flap.

9. The diaper sheath of claim 1, wherein said back portion of the inner panel has a back opening.

10. The diaper sheath according to claim 9, further comprising a back flap attached to said back portion of said inner panel and covering said back opening.

11. The diaper sheath of claim 10, wherein said intermediate strips and the intermediate pocket openings are covered by said back flap.

12. The diaper sheath of claim 1, wherein the slide is a spring-loaded stopper and each intermediate strip is inserted through a respective stopper so that the position of the intermediate strip can be continuously adjusted.

13. The diaper sheath of claim 12, wherein the stoppers are placed within the intermediate pocket or disposed at the opening of the intermediate pocket.

14. The diaper sheath of claim 1, wherein said inner panel comprises a laminated liquid permeable material and said outer panel comprises a laminated liquid impervious material.

15. The diaper sheath of claim 14, wherein said laminated liquid impervious material is a layer of laminated organic cotton on the outer surface of the outer panel.

16. The diaper sheath according to claim 14, wherein said inner panel is constructed of fleece material made of 100% polyester.

17. The diaper sheath of claim 1, further comprising a back elastic strip attached to said inner and outer panels along the edge of said back portion.

18. The diaper sheath of claim 1, wherein the first and second intermediate strips are selected from the group consisting of elastic band, string, rope or thread.

19. The diaper sheath of claim 18, wherein said first and second intermediate strips are each a solid elastic band.

20. The diaper sheath of claim 1, further comprising two measuring indicators, each disposed on a respective intermediate strip.

21. The diaper sheath according to claim 20, wherein said measuring indicator is selected from the group consisting of scale marks, numbers or letters.

22. The diaper sheath of claim 1, further comprising a pad fully or partially inserted between said inner and outer panels.

23. The diaper according to claim 22, wherein said pad is a removable, reusable, absorbent pad.

24. The diaper according to claim 22, wherein said pad is disposable.

25. A diaper comprising:
- a shell having an inner panel and an outer panel, each of said inner and outer panels having a front portion and a back portion, each of said panels attached peripherally one to the other in matched contour to form a front edge, a back edge, and a first side edge and a second side edge;
- a first intermediate pocket and a second intermediate pocket set along the first side edge and the second side edge, respectively, each intermediate pocket having an opening; and
- a first intermediate strip and a second intermediate strip set inside each of the first and second intermediate pockets, respectively, the first and second intermediate strips each having an anchor portion attached to an attachment ring, and an elongated portion having a loop formed through a slide, the loop passing through the attachment ring and having a continuously adjustable length selected by moving the slide to a desired position along the elongated portion, the first and second intermediate strips being disposed within each of the first and second intermediate pockets so as to be temporarily removable from the respective pocket to facilitate adjustment.

* * * * *